United States Patent [19]

Genese

[11] 4,226,236
[45] Oct. 7, 1980

[54] PREFILLED, VENTED TWO-COMPARTMENT SYRINGE

[75] Inventor: Joseph N. Genese, Waukegan, Ill.

[73] Assignee: Abbott Laboratories, North Chicago, Ill.

[21] Appl. No.: 36,927

[22] Filed: May 7, 1979

[51] Int. Cl.³ .............................................. A61M 5/00
[52] U.S. Cl. ............................ 128/218 M; 128/272.1
[58] Field of Search ............... 128/218 M, 272.1, 215, 128/216, 234, 218 D, 218 DA, 218 R, 218 P, 235

[56] References Cited

U.S. PATENT DOCUMENTS

| 2,591,046 | 4/1952 | Brown | 128/218 M |
|---|---|---|---|
| 2,896,622 | 7/1959 | Huttermann | 128/272 |
| 3,330,282 | 7/1967 | Visser et al. | 128/272.1 |
| 3,477,431 | 11/1969 | Walecka | 128/218 M |
| 3,757,779 | 9/1973 | Rovinski | 128/218 M |
| 3,889,674 | 6/1975 | Cilento | 128/218 M |

FOREIGN PATENT DOCUMENTS 49-10657 4/1974 Japan ................................ 128/218 M

*Primary Examiner*—John D. Yasko
*Attorney, Agent, or Firm*—Robert L. Niblack; Neil E. Hamilton

[57] ABSTRACT

A prefilled, readily activated syringe assembly wherein a fluid medicament and a diluent therefor can be intermixed in a syringe barrel with a venting thereof. A medical powder is sealed in a barrel by means of an intermediate slidable stopper and the diluent is sealed in the same barrel between the stopper and a plunger stopper. A bypass channel is provided in the syringe barrel which permits intermixing of the diluent and the medicament when the plunger stopper is moved toward the intermediate stopper. Movement of the plunger stopper inwardly in the barrel is afforded by means of a hydrophobic filter element associated with the nozzle portion. After intermixing of the diluent and the medicament the filter vent is pierced by means of a piercing tubular member to which is attached a hypodermic needle. Continued movement of the plunger stopper will expel the mixed medicament from the syringe.

16 Claims, 6 Drawing Figures

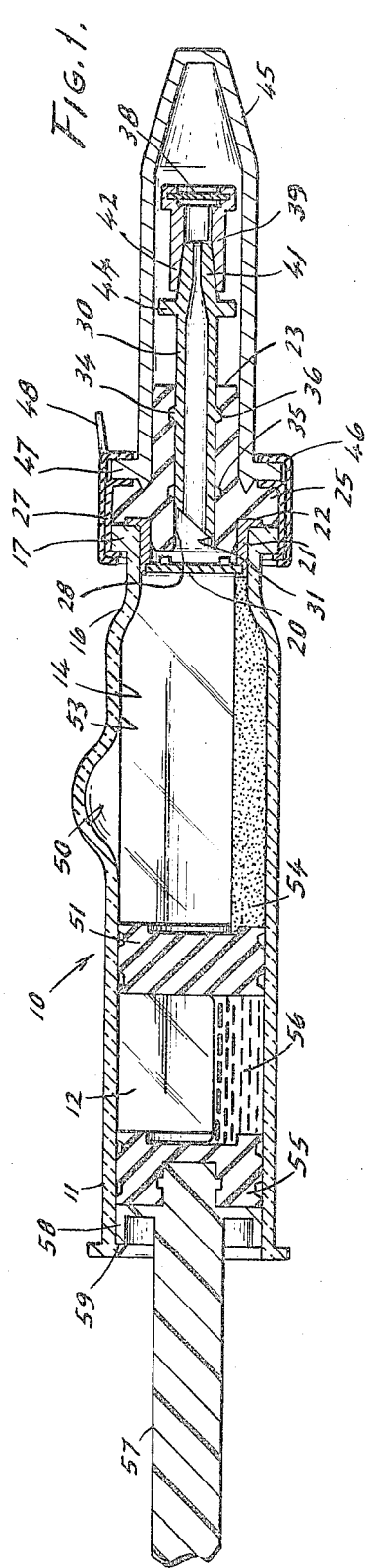
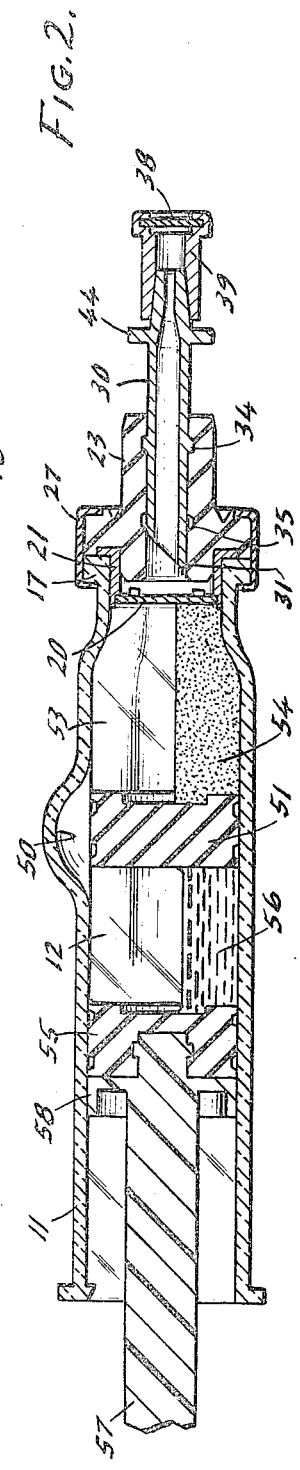
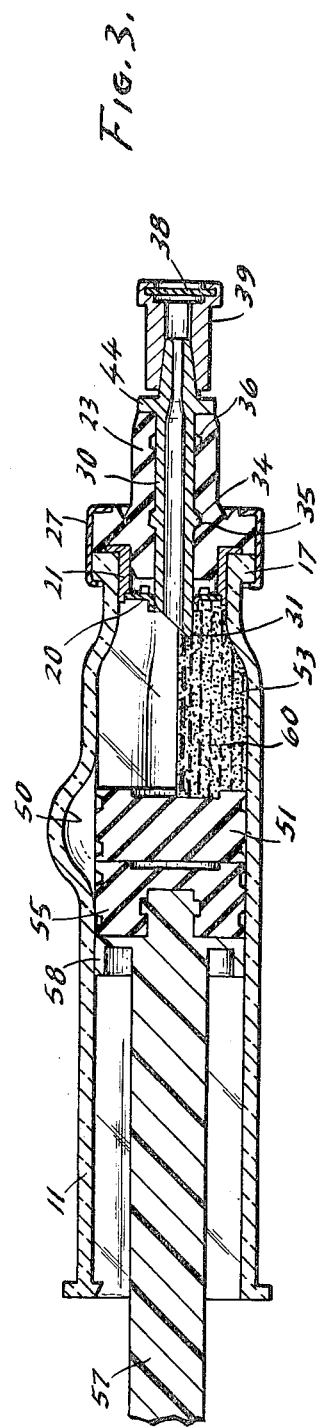

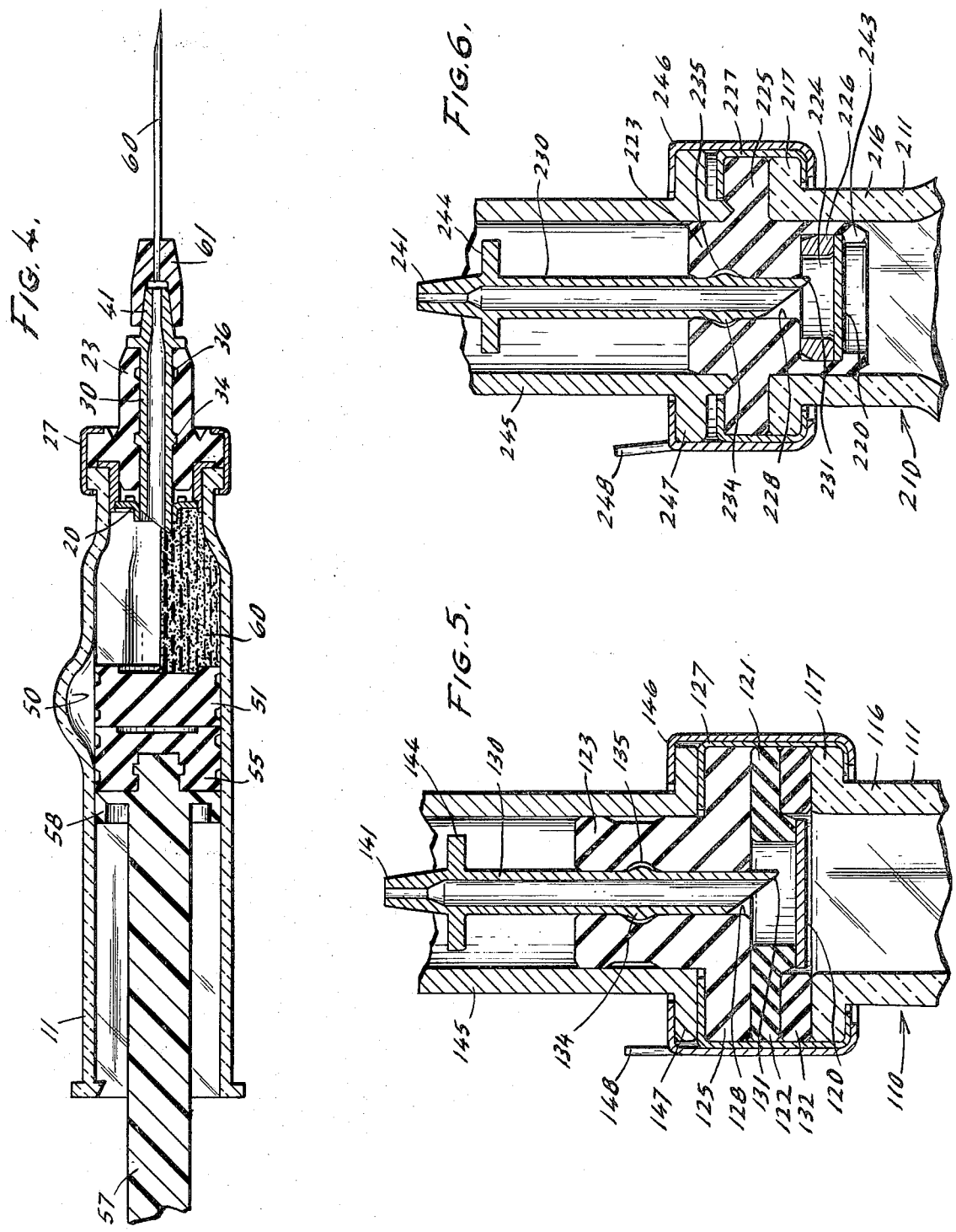

PREFILLED, VENTED TWO-COMPARTMENT SYRINGE

BACKGROUND OF THE INVENTION

This invention relates to a disposable syringe of the prefilled type. More particularly, it relates to a prefilled, disposable syringe assembly wherein the medicament and diluent are contained in the syringe and separated by an intermediate slidable stopper. When it is desired to mix the components, a plunger stopper is moved toward the intermediate stopper with the intermediate stopper being moved adjacent a bypass channel formed in the syringe barrel. This permits intermixing of the components. Undesired compression of air in the syringe barrel is vented by means of a hydrophobic filter positioned in the nozzle portion. To administer the contents of the syringe, the filter is pierced by a piercing tubular member to which is attached a hypodermic needle.

There are currently available many types of disposable syringes wherein a medicament is sealed in the syringe barrel to be later combined with a diluent for the material with the syringe barrel having a bypass channel. Such syringe types are described in U.S. Pat. Nos. 2,896,622; 3,330,282; 3,477,431; 3,899,674 as well as Japanese Registration No. 1065744. There are also available wet/dry syringe systems wherein a filter is utilized in the syringe barrel to filter the contents prior to delivery. For example, in U.S. Pat. No. 3,757,779 an intermixing type syringe with a filter is disclosed. However, the prior art does not afford a wet/dry syringe system wherein intermixing of the wet and dry components can be effected in a single syringe barrel which is vented by means of a hydrophobic filter.

It is an advantage of the present invention to provide a novel preassembled mixing and hypodermic needle assembly which affords a venting of the syringe during the intermixing of the components. Other advantages are a syringe which is completely preassembled, a syringe which utilizes a hydrophobic filter as a vent means and a pointed tubular or cannula member for piercing through the filter for delivery of the mixed materials, and a syringe which affords intermixing of dry and wet materials in a single syringe barrel.

SUMMARY OF THE INVENTION

The foregoing advantages are accomplished and the shortcomings of the prior art are overcome by the prefilled, readily activated syringe assembly of this invention which has a barrel member with the usual nozzle portion. A hydrophobic filter is positioned in or adjacent the nozzle portion as well as a holder member for a piercing tubular member which holds the piercing member in a slidable manner. A first stopper is positioned in slidable and sealing engagement in the tubular syringe barrel to provide a compartment for a first flowable medicinal material. A plunger stopper is spaced from the first stopper to provide a second chamber for a liquid diluent for the flowable medicinal material in the first chamber. A bypass means is disposed in the barrel wall and the first stopper is spaced from the bypass opposite the nozzle portion. Upon movement of the plunger stopper toward the first stopper, the first stopper will move adjacent the bypass channel to permit intermixing of the two materials with emission of air through the filter element. Upon subsequent movement of the piercing member toward the filter, the filter is pierced. The mixed contents of the syringe is delivered by attachment of a hypodermic needle to the piercing tubular member and movement of the plunger stopper toward the first stopper. In a preferred manner, the piercing member is retained in the holder member by means of a slidable frictional engagement arrangement provided by projections on the tubular member and accommodating grooves in the holder. A removable second filter element is placed on the end of the holder member opposite the piercing point for subsequent placement thereon of a hypodermic needle. A removable closure means is positioned over the holder member and secured to the nozzle portion as is the holder member.

BRIEF DESCRIPTION OF THE DRAWING

A better understanding of the prefilled, vented, readily activated syringe of this invention will be afforded by reference to the drawing wherein:

FIG. 1 is a view in vertical section showing the hypodermic syringe of this invention in a packaged condition.

FIGS. 2 and 3 are views similar to FIG. 1 showing the unit in the next stages of operation.

FIG. 4 is a view similar to FIG. 1 showing the syringe unit with the two components completely mixed and ready for injection.

FIGS. 5 and 6 are partial views in vertical section showing alternative embodiments of the syringe unit.

DESCRIPTION OF THE PREFERRED EMBODIMENT

The prefilled, vented, readily activated syringe generally 10 is composed of a barrel 11 forming a tubular chamber 12 with internal wall 14. A nozzle portion 16 extends from one end of the syringe barrel and includes a flange 17. Positioned in nozzle portion 16 is a hydrophobic filter 20 which is retained therein by means of an annular support 21 with a flange section 22 for seating on barrel flange 17. A holder member 23 is in sealing engagement with the nozzle portion 16 and includes a shoulder section 25 for holding the flange section 22 of support 21 against flange 17. The usual ferrule 27 secures shoulder 25 to flange 17 with flange 22 therebetween. A passage 28 is provided in holder 23 in which is slidably received a piercing tubular member 30 having a piercing point 31. Projection 34 is accommodated by groove 36 to afford a frictional engagement of piercing member 30 in holder 23. A second filter 38 disposed in a cap housing 39 is placed on the end of tubular member 30 opposite point 31. A male luer portion 41 on tubular member 30 and a female luer portion 42 in the cap housing 39 provides the necessary interfitment. A flange portion 44 extends from piercing member 30 adjacent luer portion 41. Positioned over piercing member 30 and filter 38 is a removable closure cap 45 which is fastened to flange 17 by a second ferrule 46 engaging shoulder 47. A pull-tab 48 provides the usual means of removal.

Referring specifically to FIG. 1, it will be seen that syringe barrel 11 includes a lateral extension or bypass channel 50 formed as part of the barrel. A stopper 51 is sealably positioned in barrel 11 and spaced from bypass channel 50 to provide a chamber 53 for a solid medicament 54. A second stopper 55 is also sealably positioned in barrel 11 and spaced from stopper 51 to provide a chamber 12 for a liquid diluent 56. A plunger rod 57 engages stopper 55 and has an annulus 58 for contact with a stop surface 59. Referring specifically to FIG. 4, it will be noted that prior to delivery of the mixed contents of the syringe 10, filter 38 and cap housing 39 will be replaced with hypodermic needle 60 which through adapter hub 61 is positioned on male luer portion 41.

FIGS. 5 and 6 illustrate various modifications for securing a venting filter to the syringe barrel as well as for the frictionally slidable arrangement of the tubular piercing member in the holder. Similar numbers are used to indicate similar parts except that they are designated in the "100" and "200" series. In the FIG. 5 unit, it will be noted that filter 120 is housed outside the confines of nozzle portion 116 and is attached to support 121 which is sealed to flange 117 by an annular sealing ring 132. It will be further noted that in conjunction with units 110 and 210 that only single grooves 135 and 235 are employed with projections 134 and 234 as the slidable frictional engagement means for tubular members 130 and 230, respectively. Syringe assembly unit 210 differs from units 10 and 110 in that a compartment or chamber 224 is disposed in holder member 223 for retention of filter 220. A retaining ring 226 provides a secure fitment by forcing filter 220 against abutment 243.

Operation

A better understanding of the advantages of the readily activated syringe units 10, 110 and 210 will be had by a description of the manner of their operation. Referring to syringe unit 10, it will be packaged as shown in FIG. 1. The medicinal material 54 will in this instance be a powdered, flowable material such as a general anesthetic. It will be noted that the medicinal material will be held in a sterile condition by means of sealing stopper 51 which is positioned in barrel 11 away from bypass channel 50 and opposite nozzle portion 16. A liquid diluent 56 will similarly be held in a sterile condition as it will be sealed between stopper 51 and plunger stopper 55. If desired, the entire syringe unit could be packaged in a sterile overwrap such as composed of sterile paper or aluminum laminate.

When it is desired to utilize unit 10, all that is required is removal of closure cap 45 by a pulling force on tab 48 and a breaking away of ferrule 46. Movement of plunger rod 57 inwardly into barrel 11 will be effected and will force stopper 51 to a position immediately adjacent bypass channel 50, as shown in FIG. 2. During this movement, air inside barrel 11 will tend to compress. However, such compression will be relieved through hydrophobic filter 20 and passage through tubular piercing member 30 and filter 38. Movement of stopper 55 will be continued until it abuts against stopper 51 as indicated in FIG. 3. At this stage diluent 56 will have been moved via bypass channel 50 into chamber 53 which medicament 54 to result in a mixed solution 60 of the medicament. No leakage of material from the barrel 11 will be effected because of the hydrophobic nature of the material of filter 20. The syringe will then be shaken to effect mixing of the two components. The next stage is the piercing of filter 20 by movement of piercing member 30 toward the filter until piercing point 31 penetrates therethrough and flange 44 contacts the end of holder 23 as shown in FIG. 3. At this point, filter 38 and cap housing 39 will be removed and replaced with hypodermic needle 60 and hub 61 as indicated in FIG. 4. Continued movement of plunger 55 into barrel 11 will also effect a corresponding movement of stopper 51 with a subsequent expulsion of the mixed components through hypodermic needle 60.

The functioning of syringe units 110 and 210 will be substantially the same as previously indicated for unit 10. The purpose of illustrating these embodiments is to show different methods of fabrication and placement of the pierceable hydrophobic filters 120 and 220 as well as different designs for the holders 123 and 223.

In conjunction with the previously described embodiments, it will be recognized that the needle 60 with adapter 61 could be placed on the holder 23 at the time the unit is packaged as shown in FIG. 1. However, closure cap 45 and the additional filter 38 would not be utilized. Some degree of sterility may be compromised and the needle will then have to have a vented sealing cap to cover it. Further, while a bypass channel 50 and double stopper system is utilized as a means of effecting a mixing of the diluent 56 with powder 54, the pierceable hydrophobic vent system of this invention would be operable with any wet/dry mixing syringe where internal pressure is a problem in resisting stopper movement.

The preferred materials for composing barrels 11, 111 and 211 is glass. However, they could be formed from other clear or translucent plastic materials such as polypropylene and polymethylpentene polymers. Stoppers such as 51 and 55 are formed from a resilient rubber or plastic material. Hydrophobic filters 10, 38, 120 and 220 are fabricated from a porous acrylic copolymer material. However, any substance which will repel the diluent to be used with the medicament can be employed if it lends itself to fabrication as a filter material. Tubular piercing members 30, 130 and 230 are preferably formed from a polycarbonate material whereas holder members 23, 123 and 223 can be conveniently fabricated from a resilient rubber or plastic material.

It will thus be seen that through the present invention there is now provided a prefilled, vented, readily activated, sterile syringe assembly which can be packaged in a ready-to-use manner and involves a minimum number of manipulative steps for utilization. A medicament material and a diluent therefor, which when intermixed result in a unstable product, are retained in a sterile condition in an isolated manner. Positive, sequential operation of the dual component syringe system is afforded by means of a unique filter, venting and delivery system to effect mixing of the medicament and the diluent as well as delivery thereof. The syringe unit can be fabricated without expensive molding operations and can be assembled in a convenient manner and retained in a sterile condition.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A prefilled, vented, readily activated syringe assembly adapted to receive a hypodermic needle comprising:
   a barrel member defining a substantially tubular chamber having a wall portion;
   a nozzle portion communicating with said tubular chamber;
   a hydrophobic filter element operatively associated with said nozzle portion of said barrel member;

a holder member in sealing arrangement with said nozzle portion and positioned outwardly from said filter element;

means to retain said holder member on said nozzle portion;

passage means defined by said holder element;

a piercing tubular member having a piercing point, slidably positioned in said passage means of said holder member and said piercing point spaced from said filter element;

a first stopper in slidable and sealing engagement in said tubular chamber to provide a compartment for a first flowable medicinal material;

a second stopper adapted to receive a plunger rod in slidable and sealing engagement in said tubular chamber of said barrel member and spaced from said first stopper to provide a compartment for a second flowable medicinal material;

means constructed and arranged in combination with said first and second stoppers and said barrel member to provide upon movement of said first stopper toward said second stopper fluid communication between said compartments for said first and second medicinal materials;

whereby upon movement of said second stopper in the direction of said first stopper, intermixing of said first and second medicinal materials will be effected with emission of air through said filter element; upon subsequent movement of said piercing tubular member toward said filter with a piercing thereof; attachment of said hypodermic needle to said piercing tubular member; and upon further movement of said second stopper toward said first stopper substantially; all of said medicinal materials will be expelled from said syringe.

2. The prefilled, vented, readily activated syringe assembly as defined in claim 1 further including a second filter element secured to said piercing tubular member at an end opposite said piercing point.

3. The prefilled, vented, readily activated syringe assembly as defined in claim 2 wherein said piercing tubular member defines a male luer adapter portion for attachment to said second filter element and said hypodermic needle.

4. The prefilled, vented, readily activated syringe assembly as defined in claim 2 wherein said holder member is composed of a resilient material and said passage means and said piercing tubular member defines a slidable frictional engagement means for said piercing tubular member.

5. The prefilled, vented, readily activated syringe assembly as defined in claim 4 wherein said slidable frictional engagement is defined by at least one projection extending from said piercing tubular member and an accommodating groove in said holder member.

6. The prefilled, vented, readily activated syringe assembly as defined in claim 1 wherein said piercing tubular member includes a flange for contact with said holder member after said piercing point pierces said hydrophobic filter element.

7. The prefilled, vented, readily activated syringe assembly as defined in claim 5 wherein said nozzle portion defines a flange portion, said syringe assembly includes an annular support with a flange section seated on said flange portion of said nozzle portion, said hydrophobic filter element is secured to said annular support and said holder member includes a shoulder section for holding said flange section of said annular support against said flange portion of said nozzle portion.

8. The prefilled, vented, readily activated syringe assembly defined in claim 7 wherein said annular support is dimensioned to position said filter element within the confines of said nozzle portion.

9. The prefilled, vented, readily activated syringe system as defined in claim 7 further including an annular sealing element positioned between said flange section of said annular support and said flange portion of said nozzle portion and said filter element is positioned outside the confines of said nozzle portion.

10. The prefilled, vented, readily activated syringe assembly as defined in claim 5 wherein said nozzle portion defines a flange portion, said holder member includes a shoulder for seating on said flange portion and a compartment for housing said filter element and said syringe assembly includes a filter retaining member for seating in said compartment and retaining said filter therein.

11. The prefilled, vented, readily activated syringe assembly as defined in claims 7 or 10 further including removable closure means for surrounding said holder member for securing said closure means to said flange portion of said nozzle portion.

12. A prefilled, vented, readily activated syringe assembly adapted to receive a hypodermic needle comprising:

a barrel member defining a substantially tubular chamber having a wall portion with a bypass channel formed in said wall portion;

a nozzle portion communicating with said tubular chamber;

a hydrophobic filter element in sealing engagement with said nozzle portion of said barrel member;

a holder member in sealing engagement with said nozzle portion and positioned outwardly from said filter element;

passage means defined by said holder element;

a piercing tubular member having a piercing point, slidably positioned in said passage means of said holder member and said piercing point spaced from said filter element;

a first stopper in slidable and sealing engagement in said tubular chamber and spaced from said bypass channel opposite said nozzle portion to provide a compartment for a first flowable medicinal material;

a second stopper adapted to receive a plunger rod in slidable and sealing engagement in said tubular chamber of said barrel member and spaced from said stopper to provide a compartment for a second flowable medicinal material;

whereby upon movement of said second stopper in the direction of said first stopper, said first stopper will move adjacent said bypass channel to thereby permit intermixing of said first and second medicinal materials with emission of air through said filter element; upon subsequent movement of said piercing tubular member toward said filter with a piercing thereof; attachment of said hypodermic needle to said piercing tubular member; and upon further movement of said second stopper toward said first stopper substantially all of said medicinal materials will be expelled from said syringe.

13. The prefilled, vented, readily activated syringe assembly as defined in claim 12 further including a second hydrophobic filter element secured to said piercing tubular member at an end opposite said piercing point.

14. The prefilled, vented, readily activated syringe assembly as defined in claim 13 wherein said first flowable medicinal material is solid material in powder form and said second material is a liquid.

15. The prefilled, vented, readily activated syringe assembly as defined in claim 14 further including a removable closure means positioned over said holder member and secured to said nozzle portion.

16. The prefilled, vented, readily activated syringe assembly as defined in claim 15 wherein said syringe barrel is formed from glass and all of said other components are formed from materials other than glass.

* * * * *